US011364477B2

(12) United States Patent
Pedersen et al.

(10) Patent No.: US 11,364,477 B2
(45) Date of Patent: Jun. 21, 2022

(54) THERMOLYTIC FRAGMENTATION OF SUGARS USING RESISTANCE HEATING

(71) Applicant: HALDOR TOPSØE A/S, Kgs. Lyngby (DK)

(72) Inventors: Lars Storm Pedersen, Farum (DK); Morten Boberg Larsen, Smørum (DK); Peter Mølgaard Mortensen, Roskilde (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 17/252,000

(22) PCT Filed: Jul. 16, 2019

(86) PCT No.: PCT/EP2019/069073
§ 371 (c)(1),
(2) Date: Dec. 14, 2020

(87) PCT Pub. No.: WO2020/016209
PCT Pub. Date: Jan. 23, 2020

(65) Prior Publication Data
US 2021/0260549 A1    Aug. 26, 2021

(30) Foreign Application Priority Data
Jul. 16, 2018    (DK) .......................... PA 2018 00393

(51) Int. Cl.
*C07C 29/14*    (2006.01)
*C07C 45/60*    (2006.01)
*B01J 6/00*    (2006.01)

(52) U.S. Cl.
CPC ............... *B01J 6/008* (2013.01); *C07C 29/14* (2013.01); *C07C 45/60* (2013.01)

(58) Field of Classification Search
CPC ........... C07C 29/14; C07C 45/60; B01J 6/008
See application file for complete search history.

(56) References Cited

U.S. PATENT DOCUMENTS

| 4,904,452 A | 2/1990 | Acharya et al. |
| 5,952,029 A | 9/1999 | Freel |
| 7,094,932 B2 | 8/2006 | Majerski et al. |
| 2010/0162625 A1 | 7/2010 | Mills |
| 2012/0202994 A1 | 8/2012 | Friese et al. |
| 2012/0214113 A1 | 8/2012 | Kulprathipanja et al. |
| 2014/0318944 A1 | 10/2014 | Baird et al. |
| 2018/0312410 A1 | 11/2018 | Taarning et al. |

FOREIGN PATENT DOCUMENTS

| JP | S48097861 A | 12/1973 |
| JP | H06506361 A | 7/1994 |
| JP | 2011506072 A | 3/2011 |
| JP | 2015-105344 A | 6/2015 |
| WO | 9111499 A1 | 8/1991 |
| WO | 9217076 A1 | 10/1992 |
| WO | 9943768 A1 | 9/1999 |
| WO | 2016001169 A1 | 1/2016 |
| WO | 2017064267 A1 | 4/2017 |
| WO | 2017216311 A1 | 12/2017 |

OTHER PUBLICATIONS

First Office Action—Search Report dated Feb. 18, 2021, issued by the Danish Patent and Trademark Office in corresponding Danish Patent Application No. PA 2020 01345. (10 pages).
Second Office Action—Second technical examination dated Aug. 24, 2021, issued by the Danish Patent and Trademark Office in corresponding Danish Patent Application No. PA 2020 01345. (3 pages).
Danish Patent Search Report dated Nov. 22, 2018.
International Search Report (PCT/ISA/210) dated Oct. 23, 2019, by the European Patent Office as the International Searching Authority for International Application No. PCT/EP2019/069073.
Written Opinion (PCT/ISA/237) dated Oct. 23, 2019, by the European Patent Office as the International Searching Authority for International Application No. PCT/EP2019/069073.
Office Action (Notice of Reasons for Refusal) dated Nov. 4, 2021, by the Japanese Patent Office in corresponding Japanese Patent Application No. 2021-501033, and an English Translation of the Office Action. (8 pages).
Office Action (Communication pursuant to Article 94(3) EPC) dated Dec. 11, 2021, by the European Patent Office in corresponding European Application No. 19 742 172.0-1109. (5 pages).

*Primary Examiner* — Sikarl A Witherspoon
(74) *Attorney, Agent, or Firm* — Buchanan Ingersoll & Rooney P.C.

(57) ABSTRACT

A process for large scale and energy efficient production of oxygenates from sugar is disclosed in which a sugar feedstock is introduced into a thermolytic fragmentation reactor comprising a fluidized stream of heat carrying particles which are separated from the reaction product and directed to a reheater comprising a resistance heating system.

42 Claims, 4 Drawing Sheets

THERMOLYTIC FRAGMENTATION OF SUGARS USING RESISTANCE HEATING

TECHNICAL FIELD

Embodiments of the present invention relate to a process for converting a sugar feedstock into $C_1$-$C_3$ oxygenates and a system suitable for performing the process, wherein the heat carrying particles are used for providing heat to the thermolytic fragmentation of the sugar and the spent heat carrying particles are reheated in a reheater equipped with a resistance heating system. The process and the system are suitable for industrial application, and the process may be performed as a large scale, continuous process.

BACKGROUND

Biomass is of particular interest as a raw material due to its potential for supplementing and possibly replacing petroleum as a feedstock for the preparation of commercial chemicals. In recent years, various technologies for exploiting biomass have been investigated. Carbohydrates represent a large fraction of biomass, and various strategies for their efficient use as a feedstock for the preparation of commercial chemicals are being established. These strategies include various fermentation-based processes, pyrolysis, and other processes, such as hydrogenolysis, hydroformylation or acid catalyzed dehydration.

Examples of chemicals produced from biomass include: substitute natural gas, biofuels, such as ethanol and biodiesel, food browning materials, and commercial chemicals, such as diols (ethylene glycol and propylene glycol), acids (lactic acid, acrylic acid, and levulinic acid) and a wide range of other important chemical intermediates (epichlorohydrin, isoprene, furfural, and synthesis gas).

Accordingly, new uses of $C_1$-$C_3$ oxygenate products are being developed and an increasing demand for those products are expected. Such oxygenate products may e.g. be used for producing ethylene glycol and propylene glycol by subjecting the oxygenate product to hydrogenation (see, e.g., WO 2016/001169) or for scavenging hydrogen sulphide as described in WO 2017/064267. However, many other uses may be envisaged.

Several systems for converting a sugar into $C_1$-$C_3$ oxygenates by pyrolysis (also termed cracking of sugar or thermolytic fragmentation of sugar) have been proposed.

In WO 92/17076, it is suggested to provide heat indirectly using an electrical oven or directly by the combustion of natural gas or propane. Heated sand is exemplified as heat source. In the examples it seems the heat is provided using sand and that combustion of the gas takes place within the pyrolysis reactor to provide the heated sand particles.

In U.S. Pat. No. 7,094,932 the heat is provided by electrical heating through the walls of the pyrolysis reactor. In example 6, the process is scaled up, but not to industrial levels.

WO 2017/216311 discloses a reactor system comprising a separate pyrolysis reactor connected with a reheater reactor to provide a circulating fluidized bed reactor system wherein heat carrying particles are heated in the reheater to the desired temperature by conveying a combustion gas from an external combustion chamber to the reheater. The heated heat carrying particles are then recirculated to the pyrolysis reactor to provide heat for the thermolytic fragmentation of the sugar.

However, there is still a need for high yielding and more energy efficient reactor systems and processes for the preparation of sustainable $C_1$-$C_3$ oxygenates from sugars which are suitable for large scale production.

SUMMARY

The inventors of the present application—having a desire to develop an industrially applicable method for producing sustainable $C_1$-$C_3$ oxygenates—have found that a thermolytic fragmentation reactor providing the heat through electrically heated reactor walls is simply not suitable for industrial application. The limited heat flux to the reactor vapours requires an extended residence time which is highly disadvantageous for industrial application, especially for converting sugars into $C_1$-$C_3$ oxygenates. The inventors also found that having an external combustion chamber for burning methane to produce a flue gas for heating heat carrying particles in a riser reheater had some drawbacks, since a large flue gas flow was required to deliver sufficient heat to the system. The inventors of the present application surprisingly found that a multitude of significant advantages could be obtained by providing a reactor system comprising a reheater using resistance heating as heat source for heating the spent heat carrying particles in a reactor system for producing $C_1$-$C_3$ oxygenates from a sugar by thermolytic fragmentation. For industrial application it is worth noting that even a small increase in yields, selectivities and/or conversion may result in great savings.

The inventors have now developed an improved circulating fluidized bed reactor system comprising a thermolytic fragmentation reactor (also referred to as fragmentation reactor) and a reheater which is equipped with a heating system employing resistance heating for heating the heat carrying particles within the reheater.

Accordingly, a reactor system is provided for thermolytic fragmentation of a sugar into $C_1$-$C_3$ oxygenates comprising:
  a fragmentation reactor comprising heat carrying particles for supplying heat to the thermolytic fragmentation of the sugar into $C_1$-$C_3$ oxygenates, said fragmentation reactor being equipped with a fragmentation particle inlet for introducing heated heat carrying particles into the fragmentation reactor, a fragmentation particle outlet for collecting spent heat carrying particles from the fragmentation reactor, a feedstock inlet for introducing the sugar into the fragmentation reactor, a fragmentation riser comprising a fragmentation zone and allowing thermolytic fragmentation of the sugar, and a product outlet for recovering the $C_1$-$C_3$ oxygenates;
  a reheater, said reheater comprising:
    a first reheater gas inlet
    a reheater particle inlet
    a reheater particle outlet
    a reheater gas outlet
    a resistance heating system
  first flow means for conveying spent heat carrying particles from the fragmentation particle outlet to the reheater particle inlet;
  second flow means for conveying heated heat carrying particles from the reheater particle outlet to the fragmentation particle inlet;
wherein the resistance heating system comprises a heating structure of electrically conductive material, said heating structure being arranged in a heating zone within the reheater to provide heat to the heat carrying particles within the reheater.

In the present context the "heating zone" is meant to refer to the heating zone of the reheater, even though heat may be provided in other parts of the reactor system without departing from the invention. For instance the heated heat carrying particles deliver heat to the feedstock in the fragmentation zone within the fragmentation riser.

The first and second flow means should establish fluid connections from the fragmentation particle outlet to the reheater particle inlet and from the reheater particle outlet to the fragmentation particle inlet, respectively. Embodiments of the flow means include pipes or tubes wherein the particles are fluidized. The dimensions and angles of the first and second flow means should be selected to facilitate fluidization of the heat carrying particles. In order to maintain a circulating fluidized reactor system the heat carrying particles should be kept in a fluidized state in order for the stream of heat carrying particles to behave like a fluid and be circulated. Generally it is preferred to use first and second flow means which are close to vertical. It is also preferred to have angles of between 120° to 240°. Generally the diameter of the first and second flow means should be selected to obtain a bed material flux of 1-2000 kg/m2/s. Additional fluidization gas inlets may be added to first and/or second flow means.

Preferably, the first and or second flow means are equipped with fluid control means, such as valves controlling the fluid flow in the first and/or second flow means.

The materials of the reactor system should be resistant to heat and erosion.

In embodiments of the reactor system, the heating structure of electrically conductive material is connected to an electrical power supply, wherein said electrical power supply is configured to heat the heat carrying particles to a reheater exit temperature of at least 300° C. and at most 900° C., such as 300-800° C., 400-700, or 500-650. The exact configuration of the heating system will depend on the dimensions of the heating structure (cross section and length) to obtain the desired resistance in the heating structure to produce the desired amount of energy. The exit temperature of the heated heat carrying particles depends on the heat flux from the heating structure to the heat carrying particles combined with the residence time of the heat carrying particles in the heating zone.

The heat carrying particles may be selected from the group consisting of sand, silica, glass, alumina, steel, and silicon carbide and their Sauter mean particle size of the heat carrying particles may be in the range of from 20-400 µm, such as from 20-300, 20-200 or 20-100 µm. The Sauter mean diameter is an average of particle size defined as the diameter of a sphere that has the same volume/surface area ratio as a particle of interest.

Such a system is associated with several advantages compared to known solutions. The system is applicable in industrial production of sustainable $C_1$-$C_3$ oxygenates from sugars and offers possibilities of reducing the costs per product obtained. The system offers possibilities of reducing the size and complexity of the reheater yet providing the same amount of heat to the process as well as possibilities of simplifying the process for carrying out thermolytic fragmentation of a sugar into $C_1$-$C_3$ oxygenates resulting in cost savings. In embodiments of the reactor system, the ratio of the diameter in the heating zone of the reheater and the diameter in the fragmentation zone of the fragmentation riser may be in the range of from 1:1 to 30:1.

The reactor system according to the present application allows a reduction in the required compression of air into the reactor system. Accordingly a smaller compressor may be required than in known systems. In cases where steam is used in the reheater, the compressor may even be dispensed with to allow evaporation of water to produce the reheater fluidization gas in situ.

The reheater is a reactor which has reactor walls making up the delimitation between the inside of the reheater and the surroundings. A suitable reactor wall material is steel.

The reheater of the reactor system according to embodiments of the present invention comprises a heating system which provides heat by resistance heating. The main part, such as at least 70%, 80%, 90% or 100% of the heat is provided by a heating structure made of an electrically conductive material. An electrical current is imposed between two points of the heating structure, such that resistive heat is supplied between the two points.

The electrically conductive material of the heating structure may in embodiments according to the present invention consist of a material having an electrical resistivity in the range of from $10^{-7}$ Ω·m to $10^{-5}$ Ω·m at 20° C. The electrically conductive material of the heating structure may consist of a material providing a heat flux from the heating structure to the heat carrying particles in the range of from 500 to 500,000 W/m2. The heat flux may be regulated by adjusting the electric current and the electric voltage applied to the heating structure. The electrically conductive material may comprise metal or metal alloy comprising one or more of copper, silver, aluminum, chromium, iron and nickel. Alternatively, or in addition the electrically conductive material of the heating structure may comprise an electrically conductive ceramic material, such as a material comprising one or more of silicium carbide, molybdenum carbide, wolfram carbide, titanium nitride, molybdenum disilide, wolfram disilide; or mixtures thereof.

The resistance heating system may further comprise a protective layer covering at least 50% of the surface of the heating structure; such as at least 70, 80 or 90% of the surface of the heating structure. The protective layer may accordingly comprise a material having an electrical resistivity above $10^9$ Ω·m at 20° C., such as in the range of from $10^9$ to $10^{25}$ Ω·m at 20° C., such as a ceramic material selected from the group consisting du silicium carbide, alumina, zirconium oxide, silicon nitride and/or refractory lining.

The heating structure may have any shape. However, shapes providing mechanical and electrical stability and a fairly high surface area for supplying the heat to the heating zone of the reheater are preferred. The heating structure may be shaped as one or more rods, cylinders or plates and they may be arranged in any direction within the heating zone. If several rods, cylinders, plates or other shapes are used, then they may be connected in parallel or in series and they may be arranged in different directions. The heating structure may be connected to the electrical power supply through separate conductors or the heating structure itself may be directly connected to the electrical power supply.

The electrical power supply may be arranged within the reheater or outside the reactor walls of the reheater.

When the electrical power supply is arranged outside the reactor walls the heating structure is connected to the power supply with connectors. The heating structure may pass through the reactor walls in which case the connectors are integral with the heating structure or connectors of any intermediary conductors may pass through the reactor walls to electrically connect the heating structure to the electrical power supply. In an embodiment, the ends of the heating structure or any intermediary conductors are led through the upper part of the reactor walls. An advantage of this is that the heat carrying particles will not cover the connectors in case of closing down the reactor or otherwise stopping the fluidized stream of heat carrying particles.

When the ends of the heating structure or any intermediary conductors are led through the reactor walls, they are preferably electrically insulated from the reactor walls. They may, e.g., be arranged in a fitting comprising electrically insulating material. The fitting may be, partly, of a plastic and/or ceramic material. The term "fitting" is meant to denote a device which allows for mechanically connecting two pieces of hardware. Thereby, any pressure difference between the inside of the reheater and the surroundings may be maintained despite the perforations of the reactor wall. Non-limiting examples of the fittings may be an electrically insulating fitting, a dielectric fitting, a power compression seal, a compression fitting or a flange.

According to embodiments of the present invention the reheater has a reactor wall and the heating structure is connected to the electrical power supply through said reactor wall in fittings electrically insulating the heating structure from the reactor wall. Preferably, the heating zone is arranged vertically below the reheater gas outlet. Preferably, the fittings are arranged vertically above the reheater particle outlet. Preferably, the reheater particle outlet is arranged vertically above the fragmentation particle inlet.

When referring to a first position being vertically above a second position it is to be understood that when projecting the first and second positions on a vertical axis pointing towards the center of gravity, the first position is to be considered vertically above the second position if the projection of the first position is higher on the vertical axis than the projection of the second position. Similar goes for "vertically below".

According to embodiments of the present invention the fragmentation reactor may further comprise:
- a fluidization gas inlet for introducing a fluidization gas; and/or
- a first fragmentation particle separator for separating a fraction of the spent heat carrying particles from the C1-C3 oxygenates; and/or
- a cooling section for quench cooling the C1-C3 oxygenates; and/or
- a second fragmentation particle separator for separating any remaining spent heat carrying particles from the C1-C3 oxygenates; and/or
- fragmentation stripping zone to improve mixing of any fluid passing it.

According to an embodiment, the first fragmentation particle separator is arranged within a separator vessel and the separator vessel further comprises a fragmentation stripping zone equipped with baffles or other internals to improve mixing of any fluid passing it and a separator fluidization gas inlet; wherein the stripping zone is arranged vertically below the first fragmentation particle separator and the separator fluidization gas inlet is arranged vertically below the separator stripping zone.

According to an embodiment the fragmentation particle outlet is arranged vertically below the fragmentation stripping zone and vertically above the reheater particle inlet.

According to embodiments of the present invention, the reheater may further comprise:
- a reheater stripping zone equipped with baffles or other internals to improve mixing of any fluid passing it; and/or
- a second reheater gas inlet for providing an oxidizing gas to the stripping zone of the reheater; and/or
- a reheater particle separator; and/or
- a reheater compressor.

According to an embodiment, the reheater stripping zone is arranged vertically below the heating zone and vertically above the reheater particle outlet.

The reactor system according to the present invention may advantageously be used in a process for carrying out a thermolytic fragmentation of a sugar into $C_1$-$C_3$ oxygenates, said process comprising the steps of:
a. providing heated heat carrying particles being suitable for fluidization;
b. introducing the heated heat carrying particles into a fragmentation reactor through a fragmentation particle inlet to produce a fluidized stream of particles in a fragmentation riser of the fragmentation reactor, the riser comprising a fragmentation zone;
c. providing a feedstock comprising a sugar;
d. introducing the feedstock into the fluidized stream of particles;
e. allowing the sugar to undergo a thermolytic fragmentation to produce a particle dense fragmentation product comprising the $C_1$-$C_3$ oxygenates formed;
f. separating a fraction of the heat carrying particles from the particle dense fragmentation product to produce spent heat carrying particles and a particle lean fragmentation product comprising the $C_1$-$C_3$ oxygenates formed;
g. recovering the $C_1$-$C_3$ oxygenates,
h. withdrawing the spent heat carrying particles separated in step f) from a fragmentation particle outlet in the form of a first stream of heat carrying particles and conveying this first stream of heat carrying particles via a first flow means followed by supplying the first stream of heat carrying particles to a reheater through a reheater particle inlet;
i. allowing the heat carrying particles to absorb heat within the reheater in a heating zone to produce heated heat carrying particles:
j. withdrawing the heated heat carrying particles produced in step i) from a reheater particle outlet in the form of a second stream of heat carrying particles and conveying this second stream of heat carrying particles via a second flow means followed by supplying the second stream of heat carrying particles to the fragmentation reactor through the fragmentation particle inlet; and then
k. repeating the steps c) to k).

The heat carrying particles are fluidized in both the fragmentation reactor and the reheater. Preferably the heat carrying particles are also fluidized in the first and second flow means. Such a system may be referred to as a circulating fluidized bed reactor system (CFB). In an embodiment the reactor system is a circulating fluidized bed reactor system. The superficial gas velocity in each reactor may be adjusted individually; or the superficial gas velocity in each reactor may be adjusted in concert. In an embodiment, the superficial gas velocity is at least 3 times higher in the fragmentation reactor than in the reheater, such as at least 5 or 10 times higher. In general, the fluidization is obtained by introducing a fluidizing gas and/or by any gas formed within the reactors, e.g., water being heated and evaporating into a vapor phase. In an embodiment, the superficial gas velocity of the reheater is in the range of from 0.01 m/s to 2 m/s. In an embodiment, the superficial gas velocity in the fragmentation zone of the fragmentation riser of the fragmentation reactor is in the range of from 3 m/s to 22 m/s.

Further aspects of the fragmentation reactor are disclosed in WO 2017/064267, which also published as US 2018/0312410. The aspects of the fragmentation reactor and the related process from US 2018/0312410 are hereby incorporated by reference.

When compared to a reheater as disclosed in WO 2017/064267, which produces heat by external combustion of, e.g., natural gas, the reheater of the reactor system according to the present application is much more attractive for industrial application. A combustion gas is avoided, which means there are very limited amounts of pollutants which need to be removed from the reheater. In addition, the release of $CO_2$ locally may be reduced. Another advantage is that a gas comprising an oxidant, such as oxygen, may be dispensed with or greatly reduced. The equipment is simpler and the size of the reheater may be reduced significantly. For instance, the requirements to air compressors, heat exchangers, air filters and flue gas cleaning, etc. are reduced. The energy efficiency is much better, since the flue gas flow is significantly smaller and hence a smaller air compressor and lesser flue gas heat loss. The flue gas may also be used in a distillation column in any downstream distillation processes.

In addition, the electricity used to supply the heat to the reheater may be derived from sustainable sources such as from wind mill energy or solar energy which improves the degree of sustainability of the end products. A further advantage of the process according to an embodiment of the present invention is that the need for air is reduced.

An advantage of heating or reheating the heat carrying particles in a reheater which is separate from the fragmentation reactor is that any organic material, such as coke, formed on the surface of the heat carrying particles may be removed by combustion without contaminating the fragmentation product and addition of oxygen to the fragmentation reactor may be avoided.

Even though the reactor system is described as two separate reactors, the two reactors may be integrated in various ways provided that each reactor is delimited by reactor walls. However, a part of or all of the reactor wall of one of them may be shared with the reactor wall of the other. In the latter case first and/or second flow means may simply constitute first and/or second apertures in the shared reactor wall providing the fluid connections between the two reactors. In an embodiment according to the present invention, the fragmentation reactor is positioned vertically above the reheater and the two reactors share a reactor wall having apertures making up the first and second flow means.

An advantage of the reactor system according to the present invention is that the heat transfer to heat carrying particles may be adjusted independently of the fluidization gas flow. When using natural gas as heat source, the combustion gas flow must be of a certain level and more heat requires an increased superficial gas velocity. Also, the resistance heated reheater does not produce NOx which is an advantage environmentally.

The C1-C3 oxygenates produced in the process according to the invention consist primarily of formaldehyde (C1), glycolaldehyde (C2), glyoxal (C2), pyruvaldehyde (C3) and acetol (C3). However, for most uses, the C2- and the C3 oxygenates are the most valuable products. The crude fragmentation product recovered from the process according to the present invention comprises a mix-ture of those C1-C3 oxygenates. This may interchangeably be referred to as a C1-C3 oxygenate mixture, a C1-C3 oxygenate product, and C1-C3 oxygenates. In an embodiment of the present invention, the fragmentation product is rich in glycolaldehyde, meaning that at least 50%, such as at least 60% or 70% by weight of the C1-C3 oxygenate mixture is glycolaldehyde. In another embodiment of the present invention, at least 50%, such as at least 60%, 70% or 80% by weight of the C1-C3 oxygenate mixture is glycolaldehyde or glyoxal. In yet another embodiment of the present invention, at least 3%, such as at least 5% or 7% by weight of the C1-C3 oxygenate mixture is pyruvaldehyde. In yet an-other embodiment of the present invention, at least 3%, such as at least 5% or 7% by weight of the C1-C3 oxygenate mixture is pyruvaldehyde or acetol.

The process according to the present invention is suitable for large scale production of C1-C3 oxygenates. Accordingly, it is suitable for processing amounts of sugar of more than 1,000 tons per year per reactor, such as more than 5,000, 10,000, 50,000, 100,000 or 1000,000 tons per year per fragmentation reactor, based on weight of dry sugar.

According to an embodiment, the heat carrying particles have a flux per cross sectional area in the heating zone of the reheater in the range of from 5 to 10,000 kg/m2/s. According to another embodiment, the superficial gas velocity in the heating zone of the reheater is in the range of from 0.01 m/s to 2 m/s.

The spent heat carrying particles may be mixed with an oxidative gas stream to oxidize any coke present on the surface of the spent heat carrying particles in the heating zone of the reheater, wherein the oxidative gas comprises oxygen in the range of from 3-21 vol. % (e.g. fed through second reheater gas inlet). The heat carrying particles may be fluidized within the reheater using a reheater fluidization gas (e.g. fed through first reheater gas inlet). The reheater fluidization gas is preferably an inert gas such as nitrogen, but it may contain other components such as an oxidizing gas. The reheater fluidization gas may e.g. comprise in the range of from 1-103 ppm of oxygen. The reheater fluidization gas may comprise 80-99.9 vol % nitrogen.

In an embodiment according to the present invention, the ratio of reheater fluidization gas fed to the reheater (Nm3/hour) to sugar fed to the fragmentation reactor (metric tonnes/hour) is in the range of from 10 to 1000, such as from 100 to 300.

In an embodiment, the temperature of the heat carrying particles withdrawn in step j) is in the range of from 300 to 800° C., such as in the range of from 400 to 800, 400-700 or 500-700° C.

Excess oxygen may be stripped from the heat carrying particles in a reheater stripping zone before step j).

The heated heat carrying particles introduced in step b) are preferably introduced at a rate sufficient to maintain a temperature of at least 250° C., such as at least 300 350, 400 or 450° C., after the thermolytic fragmentation of step e) has taken place, said rate being sufficient to obtain a fluidized stream of particles.

The process according to the present invention preferably comprises a step of quenching the particle lean fragmentation product of step e) at a temperature of at least 50° C. such that from the moment the feedstock is introduced into the fluidized stream of particles to the quench is performed, the mean residence time of the gas is maximum 5 seconds, such as maximum 3 seconds, such as maximum 2, 1, 0.8 or 0.6 seconds. Preferably, the particle lean fragmentation product is subjected to a second separation to produce a crude fragmentation product comprising the C1-C3 oxygenates.

Preferably, the feedstock comprises an aqueous solution of a sugar selected from the group consisting of sucrose, lactose, xylose, arabinose, ribose, mannose, tagatose, galactose, glucose and fructose; or mixtures thereof. Preferably, the concentration of sugar in the feedstock is between 10 and 90% by weight.

In an embodiment according to the present invention, the energy efficiency measured as percentage of energy (kW) supplied to the resistance heating system to energy (kW) supplied to the heated heat carrying particles is at least 80%, such as at least 82 to 99, or 90 to 98%. In another embodiment, the ratio of energy (kW) supplied to the resistance heating system to sugar fed to the fragmentation reactor (metric tonnes/hour) is in the range of from 800 to 2500, such as from 1100 to 2000.

According to the present invention a process is provided for the preparation of C1-C3 hydroxy compounds from a sugar comprising the steps of:
carrying out a process according to any one of claims 22 to 40; and then
subjecting the C1-C3 oxygenates to a hydrogenation process to obtain the corresponding C1-C3 hydroxy compounds.

FIGURES

DETAILED DESCRIPTION

Definitions

Figure 1:
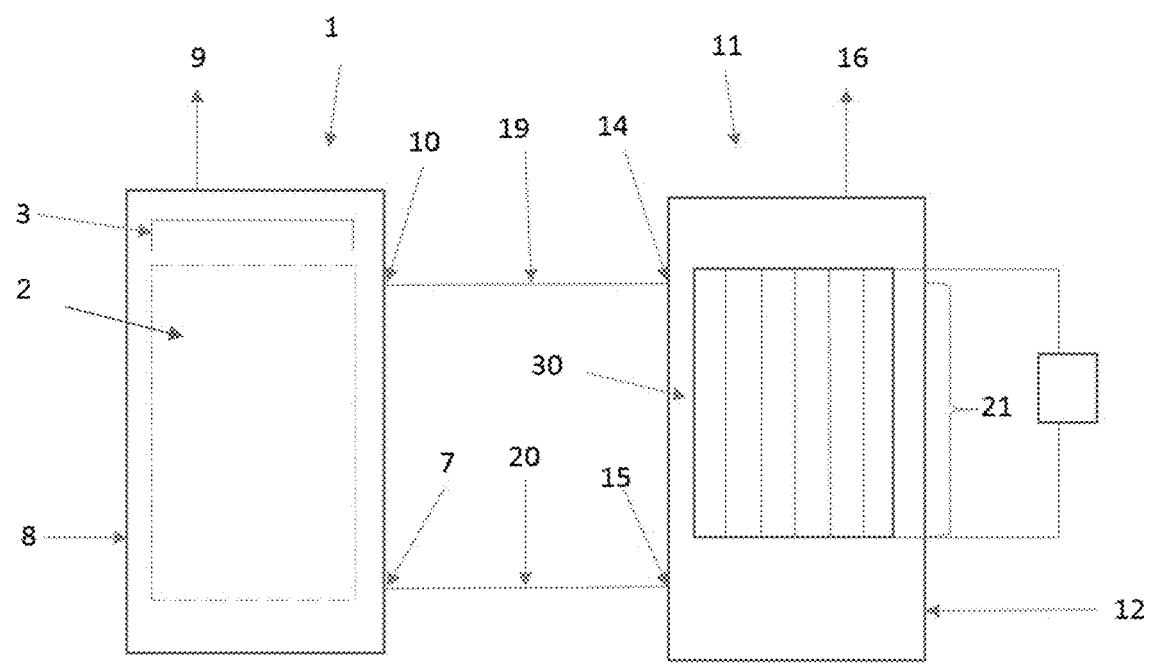
FIG. 1 is a schematic drawing of a reactor system according to an embodiment of the present invention.

When a level of at least x % is used, this inherently defines a range of from x to 100% unless stated otherwise. Similarly, when a level of below y % is used, this inherently defines a range of from 0 to y % unless stated otherwise.

Where no unit is given for a percentage, it is to be understood that the reference is per weight basis unless stated otherwise.

When referring to particle heat flux per area, then the area is defined as available are unless stated otherwise.

The term "electrically conductive" is meant to denote materials with an electrical resistivity in the range from: $10^{-7}$-$10^{-5}$ $\Omega \cdot m$ at 20° C. Thus, materials that are electrically conductive are, e.g., metals like copper, silver, aluminum, chromium, iron, nickel, or alloys comprising such metals.

The term "electrically insulating" is meant to denote materials with an electrical resistivity above 10 $\Omega \cdot m$ at 20° C., e.g. in the range from $10^9$ to $10^{25}$ $\Omega \cdot m$ at 20° C.

POSITION NUMBERS

1. Fragmentation reactor
2. Fragmentation riser
3. First fragmentation particle separator
4. Second fragmentation particle separator
5. Cooling section
6. Fluidization gas inlet
7. Fragmentation particle inlet
8. Feedstock inlet
9. Product outlet
10. Fragmentation particle outlet
11. Reheater
12. First reheater gas inlet
13. Second reheater gas inlet
14. Reheater particle inlet
15. Reheater particle outlet
16. Reheater gas outlet
17. Reheater stripping zone
18. Reheater particle separator
19. First flow means
20. Second flow means
21. Heating zone
22. First flow means control device
23. Second flow means control device
24. Fragmentation stripping zone
25. Fragmentation stripping gas inlet
30. Resistance heating system
31. Heating structure
32. Power supply
33. Fitting
34. Connector
35. Insulating material
36. Reactor wall
37. Compression fitting In embodiments of the reactor system according to the present invention, the electrically conductive material of the heating structure is a material providing an electrical resistivity in the range of from 10-5 $\Omega \cdot m$ to 10-7 $\Omega \cdot m$ at 20° C. In an embodiment, the electrically conductive material of the heating structure is a material providing a heat flux in the range of from 500 to 500,000 W/m². In an embodiment, the electrically conductive material of the heating structure is an electrically conductive metal or metal alloy comprising one or more of copper, silver, aluminum, chromium, iron and nickel. In an embodiment, the electrically conductive material comprises an Fe—Cr—Al alloy.

In embodiments of the reactor system according to the present invention, the electrically conductive material of the resistance heating system comprises a protective layer covering at least 50% of the surface of the heating structure; such as at least 70, 80 or 90% of the surface of the heating structure. In an embodiment, the protective layer comprises a material having an electrical resistivity above 10 $\Omega \cdot m$ at 20° C., such as in the range of from 109 to 1025 $\Omega \cdot m$ at 20° C. In an embodiment, the protective layer comprises a ceramic material; such as silicium carbide, alumina, zirconium oxide, silicon nitride and/or refractory lining. The protective layer is preferably an inert material. It serves to protect the heating structure of the resistance heating system. The protective layer may form a barrier against electrical current or mechanical erosion or both.

In embodiments of the reactor system according to the present invention, the reheater may have a reactor wall and the heating structure is connected to the electrical power supply through said reactor wall in a fitting so that the heating structure is electrically insulated from the reactor wall.

In an embodiment, the fragmentation reactor may further include a fluidization gas inlet for introducing a fluidization gas.

In an embodiment, the fragmentation reactor may further include a fragmentation riser comprising a fragmentation zone and allowing fragmentation.

In an embodiment, the fragmentation reactor may further include a first fragmentation particle separator for separating a fraction of the spent heat carrying particles from the $C_1$-$C_3$ oxygenates.

In an embodiment, the fragmentation reactor may further include a second fragmentation particle separator for separating any spent heat carrying particles from the $C_1$-$C_3$ oxygenates which were not separated in the first fragmentation particle separator.

In an embodiment, the fragmentation reactor may further include a cooling section for quench cooling the $C_1$-$C_3$ oxygenates.

In an embodiment, the reheater may further include a reheater stripping zone equipped with baffles or other internals to improve mixing.

In an embodiment, the reheater may further include a second reheater gas inlet for providing an oxidizing gas to the stripping zone of the reheater.

In embodiments of the process according the present invention, the heat carrying particles may be selected from the group consisting of sand, silica, glass, alumina, steel, and silicon carbide. In an embodiment, the Sauter mean particle size of the heat carrying particles is in the range of from 20-400 µm, such as from 20-300, 20-200 or 20-100 µm. In an embodiment, the heat carrying particles have a flux per cross sectional area in the range of from 5 to 10,000 kg/m²/s. However the heat carrying particles may be selected within materials having catalytic action on the fragmentation reaction without departing from this application.

In embodiments of the process according the present invention, the process may be further defined such that the superficial gas velocity of the reheater is in the range of from 0.01 m/s to 2 m/s.

In an embodiment, the spent heat carrying particles within the reheater are mixed with an oxidative gas stream to oxidize at least some of the coke present on the surface of the spent heat carrying particles, where the oxidative gas comprises oxygen in the range of from 3-21 vol. %.

In an embodiment, the heat carrying particles are fluidized within the reheater using a reheater fluidization gas comprising in the range of from 1-103 ppm of oxygen.

In an embodiment, the temperature of the heat carrying particles exiting the reheater particle outlet is in the range of from 300 to 800° C., such as in the range of from 400 to 800, 400-700 or 500-700° C.

In an embodiment, excess oxygen is stripped from the particles in a stripping zone before they are transferred from the reheater to the fragmentation reactor.

In an embodiment, the fluidized stream of particles is produced by introducing a fluidization gas, such as a nitrogen gas. In an embodiment, the fluidization gas is an inert gas.

In an embodiment, the heat carrying particles are introduced at a rate sufficient to maintain a temperature of at least 250° C., such as at least 300 350, 400 or 450° C., in the top of the fragmentation riser, said rate being sufficient to obtain a fluidized stream of particles.

In an embodiment, the process further includes a step of quenching the particle lean fragmentation product at at least 50° C. such that from the moment the feedstock is introduced into the fluidized stream of particles to when the quench is performed, the mean residence time of the gas is maximum 5, such as maximum 3 seconds, such as maximum 2, 1, 0.8 or 0.6 seconds.

In an embodiment, the process further includes subjecting the particle lean fragmentation product to a second separation to produce a crude fragmentation product comprising the $C_1$-$C_3$ oxygenates.

In an embodiment, the feedstock comprises an aqueous solution of a sugar selected from the group consisting of sucrose, lactose, xylose, arabinose, ribose, mannose, tagatose, galactose, glucose and fructose; or mixtures thereof. In an embodiment, the concentration of sugar in the aqueous solution is between 10 and 90% by weight.

The $C_1$-$C_3$ oxygenates produced may subsequently be converted into $C_1$-$C_3$ hydroxy compounds, such as by the steps of carrying out a process of thermolytic fragmentation of a sugar into $C_1$-$C_3$ oxygenates in a reactor system as described above, and then subjecting the $C_1$-$C_3$ oxygenates to a hydrogenation to obtain the corresponding $C_1$-$C_3$ hydroxy compounds.

The process according to the present invention of converting sugar into $C_1$-$C_3$ oxygenates may be controlled by control devices for controlling the gas flow to the fragmentation reactor or for controlling the gas flow to the reheater, such as valves. Also a control device may be provided for controlling the functioning of the compressor for compressing the fluidization gas to the reheater. The fluidized stream of particles in the first and/or second flow means may be controlled by control devices such as valves.

Using electric heating in the reheater for fragmentation of sugars, the only required gas in the reheater is the gas for fluidization of the heat carrying particles inside the vessel. This fluidization can be undertaken using gas spargers or gas distributor plates, known for people skilled in fluidization. Assuming operating the electrical heated reheater at 10 times minimum fluidization velocity of approximately 6 cm/s, the required gas amount for the resistance heated apparatus is approximately 60 times smaller than the reheater riser of known systems using natural gas as heat source for the reheater. In this calculation of required gas amount, only free voidage between the electrical heating pipes is accounted. In addition, the process using resistance heating is assumed to be 40% more efficient in terms of heat input per mass of sugar feed processed.

This reduced gas requirement has significant impact on the energy efficiency of the process both in terms of required net energy input and savings associated with equipment required before the thermolytic fragmentation unit.

In known fragmentation systems, the reheated heat carrying particles and reheater exit gas leaves the apparatus at the same temperature. In the known methods, the gas exiting the burner before heat exchange with spent heat carrying particles has a temperature of 1000-1400° C. The process heating efficiency, interpreted as the energy directly transferred from the source to the thermolytic fragmentation, can then roughly be calculated to be between (1000° C.–600° C.)/1000° C.*100%=40% and (1400° C.–600° C.)/1400° C.*100%=57%. The remaining energy, not directly transferred from the energy source to the thermolytic fragmentation process, leaves the process as heated gases. This energy leaving the thermolytic fragmentation with these gases is more difficult to utilize than the energy directly transferred to the fragmentation process. Since, the resistance heated thermolytic fragmentation reactor has 60 times lower gas flow exiting the regenerator, the process heating efficiency is significantly higher using resistance heating. This results in significant benefits for the environment and savings in the process.

As mentioned, there are significant savings in gas requirements comparing gas fired thermolytic fragmentation and resistance heated fragmentation. For a thermolytic fragmentation process operated at increased pressure, compression power will also be significantly higher in the case using natural gas heating, since the air requirement for the gas burner also in this case is approximately 60 times higher.

Assuming an industrial size thermolytic fragmentation reactor processing 18 tonnes per hour of dry base monosaccharide feedstock, the energy requirement of a natural gas fired reheater would be approximately 25 MW. The air requirement for such a plant would be approximately 40000-60000 m3/h. Assuming 50000 m3/h of, compression of this flow to e.g. 1.5 barg would require an electrical heat input to the compressor of 2.1 MW assuming typical compressor efficiencies. In comparison the flow of compressed gas to the resistance heated fragmentation reactor would be approximately 60 times lower or only requiring a compressor power consumption of 0.035 MW.

Figure 2:
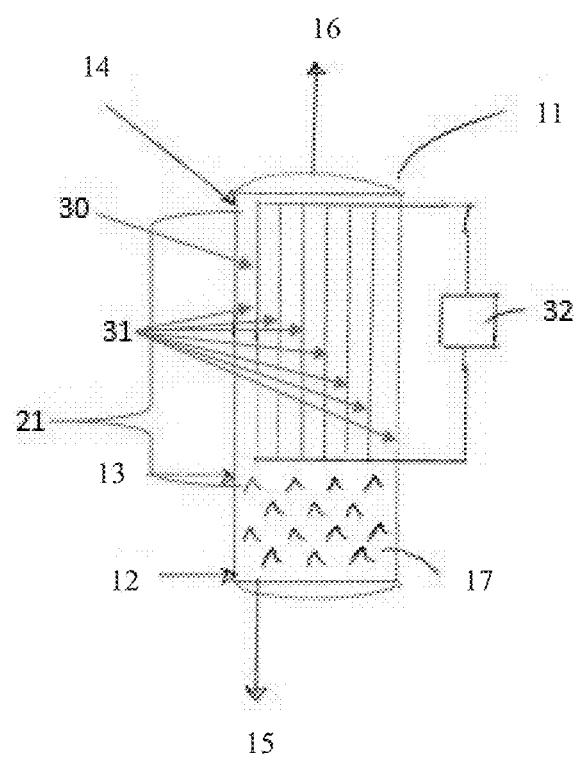
FIG. 2 illustrates one embodiment of the reheater comprising a heating zone and a stripping zone.
Figure 3A:
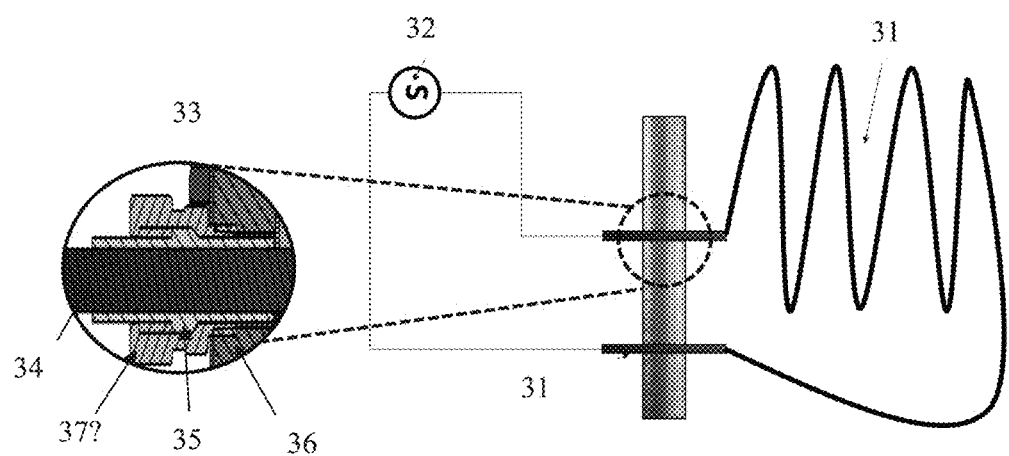
FIGS. 3A and 3B illustrate two different embodiments of fittings for leading the heating structure through the reheater wall.
Figure 3B:
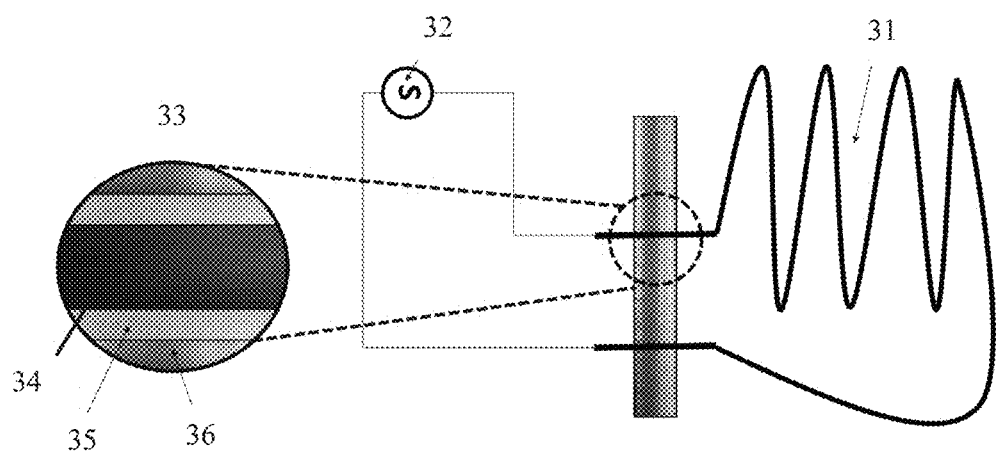
Figure 4:
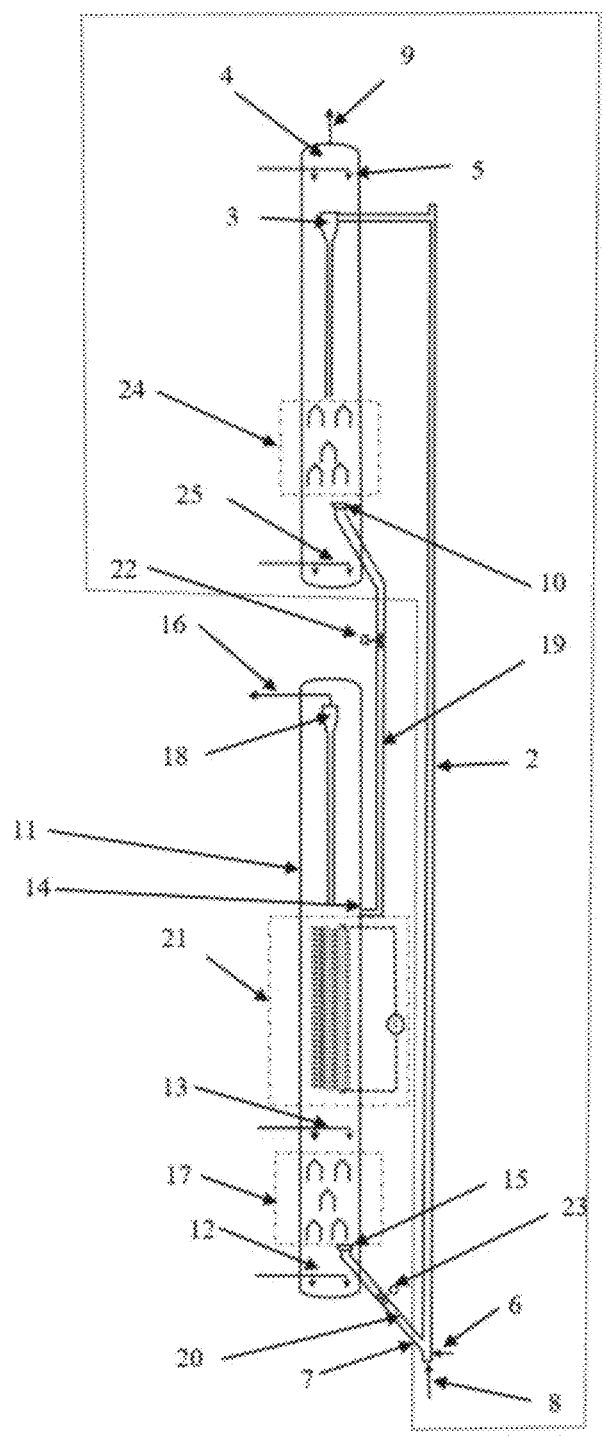
FIG. 4 illustrates an embodiment of the reactor system of the present invention, which is suitable as a circulating fluidized bed reactor system.

Schematics of the reactor and the heating structure is provided in FIG. 1-4. FIGS. 1 and 2 shows the function of the system as block type diagram and FIGS. 3 and 4 shows an example of a specific embodiment of the invention.

FIGS. 3A and 3B illustrate embodiments of the connectors connecting the heating structure with an external power supply. In 3A the heating structure 31 is connected to the power supply 32 with connectors 34. The Connectors 34 are arranged within fittings 33 passing through the reactor wall 36. FIG. 3A illustrates an embodiment where the connectors are insulated from the reactor wall by an insulator 35, which in the current embodiment is a polymer material. Sealing between the connectors and the reactor wall is ensured by a compression fitting 37, which seals any gaps in between the reactor wall 36, the insulator 35, and the connectors 34 while still having the reactor wall 36 and connectors electrically insulated from each other. FIG. 3B is a simplified version of FIG. 3A, where only the reactor wall 36, the insulator 35, and the connectors 34 are illustrating the minimum requirement of this embodiment.

Referring to FIG. 4, hot heat carrying material (also referred to as heated heat carrying particles) is transported through second flow means (20) and via fragmentation particle inlet (7) into the lower zone of the fragmentation riser (2). This lower zone of the riser is fluidized by adding gas through the fluidization gas inlet in the lower zone of the riser (6). Sugar feedstock is added through connection (8) (also referred to as feedstock inlet) and into the fluidized heat carrying material in the lower zone of the riser. The feedstock may be transformed into small droplets by means of a spray nozzle (not shown) upon injection into the lower part of the riser. After the feedstock has contacted the fluidized hot heat carrying material in the bottom of the riser, it will start to evaporate and react forming the desired products ($C_1$-$C_3$ oxygenates). During this evaporation and reaction, a significant amount of gases is formed, which increases the upward gas velocity in the riser (2) and thereby transporting the now colder heat carrying material up through the riser (2). The product gas is separated from the heat carrying particles in a first fragmentation particle separator (3). Here the first particle separator is shown to be a cyclonic device. However, it is not limited to this method, as other centrifugal or change-of-direction based separation devices can be used. The particle lean product gas from the first particle separator (3) is then rapidly cooled in cooling section (5). Here the cooling section is shown as the addition of a liquid, which upon evaporation reduces the temperature of the particle lean product gas. A secondary particle separation device (4) can be added to the unit to remove the final fraction of particles from the product gas. The secondary separation device may be based on separation principles of centrifugal separation principle, e.g. cyclones or swirl tubes etc. The product gas leaves through product outlet (9). The separated heat carrying material from (3) is admitted into a fragmentation stripping zone (24), product gas is stripped from the particle rich fraction (also referred to as particle dense fragmentation product) coming from the first particle separator (3). The stripping device may be configured in different ways known from prior art, e.g. grating trays or disc and donut. Gas for the proper action of the stripper is added through a fragmentation stripping gas inlet (25). Colder (also referred to as spent) heat carrying particles leaves through fragmentation particle outlet (10) via first flow means (19) (in this embodiment pipes) and with its flow rate controlled by first flow means control device (22) (in this embodiment a valve) and into the reheater (11) via the reheater inlet (14). In the reheater the heat carrying material is fluidized by means of a fluidization gas introduced through a first reheater gas inlet (12) and second reheater gas inlet (13). In the heating zone (21), a resistive heating structure supplies heat to the colder (spent) heat carrying material by direct contact between the resistive heating structure and the fluidized heat carrying material. In the upper part of the reheater (11), a reheater particle separator (18) is placed to separate heat carrying particles that are entrained from the fluidized reheater zone from the reheater gas. The reheater particle separator may also be of centrifugal type separator, e.g. cyclonic, as shown in the figure, but not limited to this. The reheater gas leaves the reheater through reheater gas outlet (16). Solid coke residues from the fragmentation of feedstock may be adhered to the reheater particles and this coke may be burned by addition of oxidant through the second reheater gas inlet (13). To increase the yield and efficiency of the fragmentation reactor (1), a reheater stripping zone (17) is positioned in the reheater to remove residues of any oxidizing gas from the heated heat carrying particles. The stripping device may be configured in different ways known from prior art, e.g. grating trays or disc and donut. The hot heat carrying particles leaves the reheater (11) through the reheater particle outlet (15) and via second flow means (20) (in this embodiment pipes) with its flow rate controlled by second flow means control device (23) (in this embodiment a valve).

In another embodiment it may be envisaged that the particle separator (3) is designed to be a particle separator with an integrated stripper (24) at the outlet of the separator for stripping the heat carrying material. Thereby eliminating the vessel surrounding the particle separator (3). Quenching of the product gas (5) could then be integrated to the product outlet of the particle separation device (9) or a separate device after the particle separator.

In yet another embodiment it could be envisaged that the particle separator (3) and the stripper are integrated with the reheater, such that the first flow means is an aperture in the reactor wall thereby eliminating the separate vessel surrounding the particle separator (3). The stripper (24) could then be integrated into the reheater. Quenching of the product gas (5) could then be integrated to the outlet of the particle separator (9) or a separate device after the particle separator.

Example 1

Industrial scale heat requirement to the reheater is, in one example, 25 MW. Assuming a regenerated heat carrying particles temperature of 600° C. and a temperature of the electrical heated internal of 800° C. and with an external heat transfer coefficient of 400 W/m2/K, the required surface area would be:

$$25*10^6 \text{ [W]}/((800[° \text{ C.}]-600[° \text{ C.}])*400 \text{ W/m}^2/\text{K})$$
$$=312 \text{ m}^2$$

This area can be configured in different ways. One approach, while still maintaining a reasonable electrical current, is to have rods with an outer diameter if 0.9" (26.3 mm). Using rods with an outer diameter of 26.3 mm and a design margin on area of 14%, the required number of 5 m electrical heated internals would be ca. 1000. Using a pitch of 0.1 m, the resulting inner diameter of the reheater vessel would be approximately 3.4 m. This is a relatively small size and shows the advantage and simplicity of using resistance heating of fluidized beds.

Assuming operating the electrical heated reheater at 10 times minimum fluidization velocity of 6 cm/s, the required gas amount is approximately 60 times smaller than the previously known reheater. This obviously leads to the savings indicated above. The gas flow in the electrical heated reheater may be larger, depending of coke combustion requirements.

Example 2

Assuming operating the electrical heated reheater at 10 times minimum fluidization velocity of 6 cm/s, the required gas amount is approximately 60 times smaller than the previously known reheater riser.

reasonable electrical current, is to have rods with an outer diameter if 0.9" (26.3 mm). Using rods with an outer diameter of 26.3 mm and a design margin on area of 14%, the required number of 5 m electrical heated internals would be ca. 1000. Using a pitch of 0.1 m, the resulting inner diameter of the reheater vessel would be approximately 3.4 m. This is a relatively small size and shows the advantage and simplicity of using resistance heating of fluidized beds.

The inner diameter of the reheater vessel would be approximately 2.6 m. The net effective volume of this vessel for transferring heat would be approximately 25 m3. This will in itself lead to savings in volume of installed plant and the benefits associated with this.

Example 3

Assuming operating the electrical heated reheater at 10 times minimum fluidization velocity of approximately 6 cm/s, the required gas amount for the electric heated apparatus in example 1 is approximately 60 times smaller than the reheater riser of previous patent. In this calculation of required gas amount, only free voidage between the electrical heating pipes is accounted.

In addition, the process using electrical heating is assumed to be 40% more efficient in terms of heat input per mass of sugar feed processed (see also later in example 2).

The process heating efficiency, interpreted as the energy directly transferred from the source to the thermolytic cracking process, can then roughly be calculated to be between (1000° C.–600° C.)/1000° C.*100%=40% and (1400° C.–600° C.)/1400° C.*100%=57%. The remaining energy, not directly transferred from the energy source to the thermolytic fragmentation process, leaves the process as heated gases. This energy leaving the thermolytic fragmentation with these gases is more difficult to utilize than the energy directly transferred to the fragmentation process.

Since, the electrical heated thermolytic fragmentation reactor has 60 times lower gas flow exiting the reheater, the process heating efficiency is significantly higher using electrical heating. This results in significant benefits for the environment and OPEX savings in the process.

Example 4

Assuming 50000 m3/h of, compression of this flow to e.g. 1.5 barg would require an electrical heat input to the compressor of 2.1 MW assuming typical compressor efficiencies. In comparison the flow of compressed gas to the electrical heated thermolysis reactor would be approximately 60 times lower or only requiring a compressor power consumption of 0.035 MW.

FURTHER EMBODIMENTS OF THE INVENTION

Embodiment 1. The reactor system according to claim 1, wherein the system is configured to fluidize the heat carrying particles within the reheater using a reheater fluidization gas, wherein the system is configured to operate with a ratio (a:b) of a) m$^3$/hour of the reheater fluidization gas to b) kg/hour on a dry basis of the sugar composition of 10 to 1000, such as 100 to 300.

Embodiment 2. The reactor system according to claim 1, wherein the electrically conductive material has a surface area, wherein the system is configured to operate with a ratio (a:b) of a) the surface area (m2) to b) kg/hour on a dry basis of the sugar composition of 1 to 1000, such as 10 to 100.

Embodiment 3. The reactor system according to claim 1, wherein the reheater has a mean diameter, wherein the system is configured to operate with a ratio (a:b) of a) the mean diameter (m) to b) kg/hour on a dry basis of the sugar composition of 0.01 to 1, such as 0.05 to 0.5.

Embodiment 4. The reactor system according to claim 1, wherein system has a process heating efficiency measured as percentage of energy (kW) supplied to the resistance heating system to energy (kW) supplied to the heat carrying particles of at least 80%, such as 82 to 99, or 90 to 98%.

Embodiment 5. The reactor system according to claim 1, wherein the system is configured to operate with a ratio (a:b) of a) energy (MW) supplied to the resistance heating system to b) kg/hour on a dry basis of the sugar composition of 800 to 2500, such as 1100 to 2000.

Embodiment 6. The reactor system according to claim 1, wherein the system is configured to fluidize the heat carrying particles within the reheater using a reheater fluidization gas, wherein the reheater further comprises a compressor to compress the reheater fluidization gas, wherein the system is configured to operate with a ratio (a:b) of a) energy (MW) supplied to the compressor to b) kg/hour on a dry basis of the sugar composition of 1 to 20, such as 2 to 8.

The invention claimed is:

1. A reactor system for thermolytic fragmentation of a sugar into $C_1$-$C_3$ oxygenates comprising:
   a fragmentation reactor comprising heat carrying particles for supplying heat to the thermolytic fragmentation of the sugar into $C_1$-$C_3$ oxygenates, said fragmentation reactor being equipped with a fragmentation particle inlet for introducing heated heat carrying particles into the fragmentation reactor, a fragmentation particle outlet for collecting spent heat carrying particles from the fragmentation reactor, a feedstock inlet for introducing the sugar into the fragmentation reactor, a fragmentation riser comprising a fragmentation zone and allowing thermolytic fragmentation of the sugar, and a product outlet for recovering the $C_1$-$C_3$ oxygenates;
   a reheater, said reheater comprising:
      a first reheater gas inlet
      a reheater particle inlet
      a reheater particle outlet
      a reheater gas outlet
      a resistance heating system
   first flow means for conveying spent heat carrying particles from the fragmentation particle outlet to the reheater particle inlet; and second flow means for conveying heated heat carrying particles from the reheater particle outlet to the fragmentation particle inlet;

wherein the resistance heating system comprises a heating structure of electrically conductive material, said heating structure being configured such that an electrical current is imposed between two points to supply resistive heat between the two points, wherein said heating structure is arranged in a heating zone within the reheater to provide heat to the heat carrying particles within the reheater.

2. The reactor system according to claim 1, wherein the heating structure of electrically conductive material is connected to an electrical power supply, wherein said electrical power supply is configured to heat the heat carrying particles to a reheater exit temperature of at least 300° C.

3. The reactor system according to claim 1, wherein the electrically conductive material of the heating structure is a material having an electrical resistivity in the range of from $10^{-7}$ Ω·m to $10^{-5}$ Ω·m at 20° C.

4. The reactor system according to claim 1, wherein the electrically conductive material of the heating structure is a material providing a heat flux from the heating structure to the heat carrying particles in the range of from 500 to 500,000 W/m².

5. The reactor system according to claim 1, wherein the electrically conductive material of the heating structure is an electrically conductive metal or metal alloy comprising one or more of copper, silver, aluminum, chromium, iron and nickel.

6. The reactor system according to claim 1, wherein the electrically conductive material of the heating structure is an electrically conductive ceramic material.

7. The reactor system according to claim 1, wherein the resistance heating system further comprises a protective layer covering at least 50% of the surface of the heating structure.

8. The reactor system according to claim 7, wherein the protective layer comprises a material having an electrical resistivity above $10^9$ Ω·m at 20° C.

9. The reactor system according to claim 7, wherein the protective layer comprises a ceramic material.

10. The reactor system according to claim 1, wherein the heat carrying particles are selected from the group consisting of sand, silica, glass, alumina, steel, and silicon carbide.

11. The reactor system according to claim 1, wherein the Sauter mean particle size of the heat carrying particles is in the range of from 20-400 μm.

12. The reactor system according to claim 1, wherein the reheater has a reactor wall and the heating structure is connected to the electrical power supply through said reactor wall in fittings electrically insulating the heating structure from the reactor wall.

13. The reactor system according to claim 12, wherein the heating zone is arranged vertically below the reheater gas outlet.

14. The reactor system according to claim 12, wherein the fittings are arranged vertically above the reheater particle outlet.

15. The reactor system according to claim 1, wherein the reheater particle outlet is arranged vertically above the fragmentation particle inlet.

16. The reactor system according to claim 1, wherein the first and or second flow means are equipped with fluid control means.

17. The reactor system according to claim 1, wherein the fragmentation reactor further comprises:

a fluidization gas inlet for introducing a fluidization gas; and/or a first fragmentation particle separator for separating a fraction of the spent heat carrying particles from the $C_1$-$C_3$ oxygenates; and/or a cooling section for quench cooling the $C_1$-$C_3$ oxygenates; and/or a second fragmentation particle separator for separating any remaining spent heat carrying particles from the $C_1$-$C_3$ oxygenates; and/or fragmentation stripping zone equipped with baffles or other internals to improve mixing of any fluid passing it.

18. The reactor system according to claim 17, wherein the first fragmentation particle separator is arranged within a separator vessel and the separator vessel further comprises a fragmentation stripping zone equipped with baffles or other internals to improve mixing of any fluid passing it and a separator fluidization gas inlet; wherein the stripping zone is arranged vertically below the first fragmentation particle separator and the separator fluidization gas inlet is arranged vertically below the separator stripping zone.

19. The reactor system according to claim 18, wherein the fragmentation particle outlet is arranged vertically below the fragmentation stripping zone and vertically above the reheater particle inlet.

20. The reactor system according to claim 1, wherein the reheater further comprises:

a reheater stripping zone equipped with baffles or other internals to improve mixing of any fluid passing it; and/or a second reheater gas inlet for providing an oxidizing gas to the stripping zone of the reheater; and/or a reheater particle separator; and/or a reheater compressor.

21. The reactor system according to claim 20, wherein the reheater stripping zone is arranged vertically below the heating zone and vertically above the reheater particle outlet.

22. The reactor system according to claim 1, wherein the reheater does not utilize a combustion gas.

23. The reactor system according to claim 2, wherein said electrical power supply is configured to heat the heat carrying particles to a reheater exit temperature of 400-700° C.

24. The reactor system according to claim 6, wherein the electrically conductive ceramic material is a material comprising one or more of silicium carbide, molybdenum carbide, wolfram carbide, titanium nitride, molybdenum disilide, wolfram disilide, mixtures thereof.

25. The reactor system according to claim 1, wherein the reheater further comprises a reheater stripping zone equipped with baffles or other internals to improve mixing of any fluid passing it.

26. The reactor system according to claim 1, wherein the system is configured to fluidize the heat carrying particles within the reheater using a reheater fluidization gas, wherein the system is configured to operate with a ratio (a:b) of a) m3/hour of the reheater fluidization gas to b) kg/hour on a dry basis of the sugar composition of 10 to 1000.

27. The reactor system according to claim 26, wherein the ratio (a:b) is 100 to 300.

28. The reactor system according to claim 1, wherein the electrically conductive material has a surface area, wherein the system is configured to operate with a ratio (c:d) of c) the surface area (m2) to d) kg/hour on a dry basis of the sugar composition of 1 to 1000.

29. The reactor system according to claim 28, wherein the ratio (c:d) is 10 to 100.

30. The reactor system according to claim 1, wherein the reheater has a mean diameter, wherein the system is configured to operate with a ratio (e:f) of e) the mean diameter (m) to f) kg/hour on a dry basis of the sugar composition of 0.01 to 1.

31. The reactor system according to claim 30, wherein the ratio (e:f) is 0.05 to 0.5.

32. The reactor system according to claim 1, wherein the system has a process heating efficiency measured as percentage of energy (kW) supplied to the resistance heating system to energy (kW) supplied to the heat carrying particles of at least 80%.

33. The reactor system according to claim 32, wherein the process heating efficiency is 82 to 99.

34. The reactor system according to claim 32, wherein the process heating efficiency is 90 to 98%.

35. The reactor system according to claim 1, wherein the system is configured to operate with a ratio (g:h) of g) energy (MW) supplied to the resistance heating system to h) kg/hour on a dry basis of the sugar composition of 800 to 2500.

36. The reactor system according to claim 35, wherein the ratio (g:h) is 1100 to 2000.

37. The reactor system according to claim 1, wherein the system is configured to fluidize the heat carrying particles within the reheater using a reheater fluidization gas, wherein the reheater further comprises a compressor to compress the reheater fluidization gas, wherein the system is configured to operate with a ratio (i:j) of i) energy (MW) supplied to the compressor to j) kg/hour on a dry basis of the sugar composition of 1 to 20.

38. The reactor system according to claim 37, wherein the ratio (i:j) is 2 to 8.

39. The reactor system according to claim 1, wherein the system is configured to fluidize the heat carrying particles within the reheater using a reheater fluidization gas, wherein the system is configured to operate with a ratio (a:b) of a) m3/hour of the reheater fluidization gas to b) kg/hour on a dry basis of the sugar composition of 10 to 1000,
  wherein the reheater has a mean diameter, wherein the system is configured to operate with a ratio (e:f) of e) the mean diameter (m) to f) kg/hour on a dry basis of the sugar composition of 0.01 to 1.

40. The reactor system according to claim 1, wherein the system is configured to fluidize the heat carrying particles within the reheater using a reheater fluidization gas, wherein the system is configured to operate with a ratio (a:b) of a) m3/hour of the reheater fluidization gas to b) kg/hour on a dry basis of the sugar composition of 10 to 1000,
  wherein the system is configured to operate with a ratio (g:h) of g) energy (MW) supplied to the resistance heating system to h) kg/hour on a dry basis of the sugar composition of 800 to 2500.

41. The reactor system according to claim 1, wherein the system is configured to fluidize the heat carrying particles within the reheater using a reheater fluidization gas, wherein the system is configured to operate with a ratio (a:b) of a) m3/hour of the reheater fluidization gas to b) kg/hour on a dry basis of the sugar composition of 10 to 1000,
  wherein the reheater has a mean diameter, wherein the system is configured to operate with a ratio (e:f) of e) the mean diameter (m) to f) kg/hour on a dry basis of the sugar composition of 0.01 to 1,
  wherein the system is configured to operate with a ratio (g:h) of g) energy (MW) supplied to the resistance heating system to h) kg/hour on a dry basis of the sugar composition of 800 to 2500,
  wherein the reheater further comprises a compressor to compress the reheater fluidization gas, wherein the system is configured to operate with a ratio (i:j) of i) energy (MW) supplied to the compressor to j) kg/hour on a dry basis of the sugar composition of 1 to 20.

42. The reactor system according to claim 1, wherein the reheater further comprises a reheater stripping zone equipped with baffles or other internals to improve mixing of any fluid passing it,
  wherein the system is configured to fluidize the heat carrying particles within the reheater using a reheater fluidization gas, wherein the system is configured to operate with a ratio (a:b) of a) m3/hour of the reheater fluidization gas to b) kg/hour on a dry basis of the sugar composition of 10 to 1000,
  wherein the reheater has a mean diameter, wherein the system is configured to operate with a ratio (e:f) of e) the mean diameter (m) to f) kg/hour on a dry basis of the sugar composition of 0.01 to 1,
  wherein the system is configured to operate with a ratio (g:h) of g) energy (MW) supplied to the resistance heating system to h) kg/hour on a dry basis of the sugar composition of 800 to 2500,
  wherein the reheater further comprises a compressor to compress the reheater fluidization gas, wherein the system is configured to operate with a ratio (i:j) of i) energy (MW) supplied to the compressor to j) kg/hour on a dry basis of the sugar composition of 1 to 20.

* * * * *